United States Patent [19]

Sofia

[11] Patent Number: 5,462,966
[45] Date of Patent: Oct. 31, 1995

[54] METHODS FOR THE PREVENTION AND CONTROL OF CELLULAR DAMAGE RESULTING FROM CORONARY ARTERY OCCLUSION-REPERFUSION

[75] Inventor: Robert D. Sofia, Willingboro, N.J.

[73] Assignee: Carter-Wallace Inc., New York, N.Y.

[21] Appl. No.: 138,128

[22] Filed: Oct. 15, 1993

[51] Int. Cl.6 .................................................. A61K 31/27
[52] U.S. Cl. .................................... 514/483; 560/158
[58] Field of Search ............................ 560/158; 514/483

[56] References Cited

U.S. PATENT DOCUMENTS

| | | | |
|---|---|---|---|
| 2,884,444 | 4/1959 | Berger et al. | 560/158 |
| 4,978,680 | 12/1990 | Sofia | 514/534 |
| 5,055,489 | 10/1991 | Sofia | 514/483 |

*Primary Examiner*—Glennon H. Hollrah
*Assistant Examiner*—Scott C. Rand
*Attorney, Agent, or Firm*—Kevin B. Clarke

[57] ABSTRACT

Methods for protecting warm-blooded animals against the formation of myocardial infarct through the administration of 2-phenyl-1,3-propanediol dicarbamate are disclosed.

1 Claim, No Drawings

METHODS FOR THE PREVENTION AND CONTROL OF CELLULAR DAMAGE RESULTING FROM CORONARY ARTERY OCCLUSION-REPERFUSION

The present invention relates to pharmaceutical compositions containing 2-phenyl-1,3-propanediol dicarbamate as an active component and to methods for the prevention and control of cellular damage resulting from coronary artery occlusion-reperfusion through the use of such compositions.

More particularly, the present invention relates to methods for protecting warm-blooded animals against the formation of myocardial infarct through the administration of therapeutic compositions which contain as an active ingredient 2-phenyl-1,3-propanediol dicarbamate, commonly known as felbamate.

Specifically, the present invention relates to the cardioprotective effects of felbamate against two markers of myocardial injury, namely: myocardial necrosis (infarct size) and changes in electrocardiogram (ECG) S-T segment elevation that follows occlusion-reperfusion injury.

Felbamate is a well known pharmaceutical compound having been described together with methods for its manufacture in U.S. Pat. Nos. 2,884,444 and 4,868,327.

Moreover, felbamate has demonstrated effective antiepileptic properties, U.S. Pat. Nos. 4,978,680 and 5,082,861. Further, felbamate has been found to have neuroprotective properties against hypoxic-ischemic brain injury in the prevention of hypoxic damage resulting from stroke or other cerebral ischemic event, U.S. Pat. No. 5,055,489.

One of the objects of the present invention is to provide compositions for the prevention and control of cellular tissue damage.

Another object of the present invention is to provide relatively non-toxic compositions effective to control or prevent cellular damage resulting from coronary artery occlusion-perfusion which include felbamate as an active component.

A further object of the present invention is to provide compositions for the prevention and control of cellular tissue damage which compositions are relatively non-toxic, have a high degree of effectiveness and continue to produce a therapeutic response over relatively long periods of time.

Moreover, it is an object of the present invention to provide methods for decreasing the size of infarct formation following coronary artery occlusion-reperfusion through the use of felbamate.

Accordingly, it has been found that felbamate, chemically described as 2-phenyl-1,3-propanediol dicarbamate, is a compound which has demonstrated superior properties with respect to controlling and/or preventing cellular damage resulting from coronary artery occlusion, a condition in which an artery supplying blood to the muscular walls of the heart, i.e., a coronary artery—is blocked by a blood clot— and reperfusion—the subsequent return of blood flow through the coronary arteries to the muscular walls of the heart. Such a condition usually leads to the formation of an infarct, i.e., a region of dead or dying tissue resulting from the sudden obstruction of blood circulation in the lung and heart muscle.

The cardio-protective effects of felbamate against the myocardial injury that followed coronary artery occlusion-reperfusion in the anesthetized rat is described in the following example.

EXAMPLE

Male, Sprague-Dawley rats (460–660 g) are housed in temperature controlled (20°–24° C.) and humidity monitored quarters (30–70%) which receive illumination (12 hours light/12 hours dark). All animals are allowed to become acclimated to laboratory conditions (minimum of five days) before testing. Husbandry practices and veterinary care are in accordance with the *Guide for Care and Use of Laboratory Animals* (NIH Publication No. 85–23, 1985).

The animals are anesthetized with pentobarbital (50–70 mg/kg, i.p.) and anesthesia is supplemented intravenously as required during the experimental period. The animals are maintained at a constant temperature of 37° C. by the use of water circulating heating blanket. The right femoral arteries are cannulated to monitor arterial blood pressure using the Gould-Statham Model P23Db pressure transducer. The heart rates are measured with a cardiotachometer (Grass Model 7P440) by taking the electrical signal from the systolic wave of the arterial blood pressure. The ECG and S-T segment heights are recorded via standard II limb leads using Grass Model 7D polygraphs (Grass Instruments, Quincy, Mass.) and a Buxco Electronics ECG Analyzer 105B (Buxco Electronics Inc., Troy, N.Y.). The reported S-T segment height represents the mean value of the ECG S-T segment waveforms obtained during 30 seconds of recording. The trachea are cannulated and the animals are artificially ventilated with a Harvard Rodent Ventilator (Model 683, Harvard Apparatus, South Natick, Mass.) at 54 strokes/minute (tidal volume—0.7 mL/100 gm body weight). The pericardium are opened at the fourth or fifth intercostal space and the hearts are exteriorized according to the methods of Selye et al. (1960). A 10 mm reverse cutting needle is used to place a 6/0 braided silk suture under the left main coronary arteries at points close to their origins. The hearts are repositioned within the thorax, the coronary arteries are ligated for 40 minutes and the ligatures are untied during the following 60 minutes of coronary reperfusion.

Coronary artery occlusion-reperfusion is known to induce cellular damage leading to the formation of myocardial infarct. It has also been documented that the reperfusion following coronary artery occlusion increases the intensity of myocardial cellular damage. Hearse et al., 1978 showed that reperfusion of the rat heart induced leakage of enzymes, ultrastructural injury and contracture.

The ischemic area (the area at risk) and the extent of myocardial necrosis (infarct size) are determined using the following procedures: Immediately following reperfusion, the coronary ligature is retied, the heart is excised and washed in saline, and a second ligature is tied to the occlusion site. The aorta of the heart is cannulated and an Evan's blue solution (0.25 mg/mL normal saline) is infused for one minute at a perfusion pressure of 75–90 mm Hg (Rabbit Plus peristaltic pump, Rainin Instrument Co., Woburn, Mass.). The perfused myocardium that stained blue is dissected from the unstained area at risk that had previously been excluded from blood circulation by coronary ligation. The area at risk is then sliced in 1 mm thick slices and incubated for one hour at 37° C. in triphenyltetrazolium chloride (1 mg/mL in 20 mM potassium phosphate, Sigma, St. Louis, Mo.). The heart slices are removed, blotted dry and placed into 10% neutral buffered formalin for 24 to 48 hours. The tissues are then removed and blotted dry and the necrotic tissue (grey) is carefully dissected from the viable (non-necrotic) tissue (stained red). The necrotic and viable tissues are each kept in separate plastic weighing trays (35×35 mm) under a damp towel during the separation procedure. The tissues are immediately weighed, and the percentage of myocardial necrosis (infarct size) of the area at risk is determined (infarct gm/myocardial area at risk, gm=% infarct).

The dosing schedule consists of vehicle (hydroxypropylcellulose 5%, in distilled water, 2 mL/kg body weight) or felbamate 100 or 300 mg/kg in vehicle, respectively, each administered orally on three consecutive days prior to experimental procedure. There are separate vehicle groups for each of the two felbamate groups, and they are designated as vehicle (100) and vehicle (300), respectively. Coronary artery occlusions are performed three hours after the oral administration of vehicle or felbamate on day three of the dosing schedule.

Significance was determined using the t-test for correlated means (paired t-test) or using the Student's t-test. The term "significant" represents a "P" value of 0.05 or less or as indicated.

In the present experiments vehicle groups, felbamate 100 mg/kg and felbamate 300 mg/kg are administered orally to rats for three consecutive days prior to the occlusion-reperfusion procedure. The vehicle groups consisted of hydroxypropylcellulose, 5% in distilled water. The effects of felbamate compared to vehicle are determined on the following markers of myocardial injury following occlusion-reperfusion in the anesthetized rats: the infarct size within the myocardial area at risk and the change in the ECG S-T segment elevation. The infarct size (myocardial necrosis) in the area at risk following occlusion-reperfusion in rats receiving vehicle (100) was 36.5±2.2% of the area at risk (Table 1). In the second vehicle group (300) the infarct size was 37.6±2.3% of the area at risk (Table 1). The % infarct sizes within the area at risk following vehicle (100) (36.5±2.2%) and vehicle (300) (37.6±2.3%) are not significantly different from each other (Table 1). The infarct sizes within the areas at risk following felbamate 100 mg/kg is 20.6±2.1% are significantly less ($P \leq 0.001$) than the infarct value following vehicle (100) (36.5±2.2%) (Table 2, FIG. 1). The infarct sizes within the areas at risk following felbamate 300 mg/kg 15.3±1.4% are significantly less ($P \leq 0.001$) than the infarct values following vehicle (300) (37.6±2.3%) (Table 3, FIG. 1). While the infarct sizes are smaller following felbamate 300 mg/kg (15.3±1.4%), the decrease is not significantly different from felbamate 100 mg/kg (20.6±2.1%) (Tables 2, 3; FIG. 1).

The second marker of myocardial injury measured is the ECG S-T segment elevation that follows occlusion-reperfusion in vehicle or felbamate pretreated rats. The S-T segment height was significantly ($P \leq 0.02$) elevated from baseline value during the entire occlusion-reperfusion period following pretreatment with vehicle (100) or vehicle (300) (Table 7, FIGS. 3, 4). The S-T segment elevations following vehicle (100) compared to vehicle (300) are not significantly different during the 40 minute occlusion and subsequent 10 through 30 minute reperfusion times; at the 40 through 60 minute reperfusion times following vehicle (300) the S-T segment elevations are significantly greater than vehicle (100) (Table 7).

In the vehicle (100) group there are significant increases from baseline S-T segment height during occlusion (144.4 to 189.5%), and during the reperfusion period of 60 minutes (105.5 to 139.6%) (Table 7, FIG. 3). In vehicle (300) group there are significant increases from baseline S-T segment height which persisted throughout the occlusion period (158.4–168.1%) and the reperfusion periods (167.5 to 195.3%) (Table 7, FIG. 4).

In contrast, the animals pretreated with felbamate 100 mg/kg do not show any significant changes from baseline S-T segment height during the 40 minute occlusion and subsequent 60 minute reperfusion periods (Table 8, FIG. 3). During the 60 minute reperfusion periods, the S-T segment height shows a non-significant decrease from baseline at each time point which ranged from −4.2±13.96% at 10 minutes to −13.5±13.70% at 60 minutes (Table 8, FIG. 3). The changes in S-T segment heights during occlusion and reperfusion in felbamate 100 mg/kg treated animals are all significantly less ($P \leq 0.001$) than the S-T segment elevation at comparable times following vehicle (100) (Table 8, FIG. 3).

The animals pretreated with felbamate 300 mg/kg do not show any significant changes from baseline S-T segment height during the 40 minute occlusion periods (Table 9, FIG. 4). During the 60 minute reperfusion period the S-T segment height shows a significant increase from baseline at each time point which ranged from 32.0±11.94% at 10 minutes to 59.7±28.44% at 60 minutes (Table 9, FIG. 4). The changes in the S-T segment heights during the occlusion and reperfusion periods in animals pretreated with felbamate 300 mg/kg are all significantly less ($P \leq 0.002$) than the S-T segment elevations at comparable times following vehicle (300) (Table 9, FIG. 4).

In accordance with the present invention, anesthetized rats were subjected to a 40 minute left descending coronary artery occlusion followed by a 60 minute reperfusion period. Two markers are used to assess the extent of myocardial injury following occlusion-reperfusion. One marker is the formation of myocardial necrosis (infarct size) within the area at risk that has undergone circulatory exclusion by coronary ligation. The second marker of myocardial injury is the alteration in ECG S-T segment height that occurs during the occlusion-reperfusion periods.

The foregoing examples demonstrate that coronary artery occlusion-reperfusion produced significant ischemic injury within the myocardial area at risk in anesthetized rats. The changes in infarct size following the administration of vehicle (100 or 300) are comparable with the results disclosed by Bernauer (1985) who also showed that the β-adrenoceptor blocking agents (pindolol, propranolol and metoprolol) and dexamethasone each caused a significant decrease in myocardial necrosis following coronary ligation in rats.

It has been suggested that the protective effect of β-blockers may be through their negative chronotropic actions (Bernauer, 1982, 1985a). Since increased sympathetic nerve activity has been reported to be present in ischemic hearts of rats and dogs, part of the protective mechanism of β-blockers may involve effects that lessen sympathetic nerve action (Malliani et al., 1969; Bosnjok et al., 1979). This would reduce the oxygen demand of the heart and favor an increase in coronary blood flow by a prolongation of diastole (Rasmussen et al., 1977; Raina et al., 1978; Brenauer, 1982). Since the β-blocker pindolol decreased myocardial necrosis without effecting heart rate, it would suggest that other myocardial protective mechanisms may also be operative (Bernauer, 1985).

Further support for additional or other cardioprotective mechanisms comes from the studies with iloprost, a prostacylin analog and RP 52891, a potassium channel activator. Iloprost reduced myocardial infarct size in the rabbit model of coronary myocardial ischemia-reperfusion in the absence, of a negative inotropic effect during normoxia, or of a coronary dilatory effect during ischemia (Ferrari et al., 1988), and in the absence of major hemodynamic effects (Chiariello et al., 1988). Recent studies have shown that in the isolated globally ischemic rat heart, the potassium channel activator RP 52891 has a direct cardioprotective effect which may be related to activation of the ATP-sensitive potassium channels (Grover et al., 1990).

In accordance with the present invention, it has been found that animals pretreated with felbamate had a greater formation of red formazan than animals receiving vehicle. Red formazan is used as a marker of cellular viability (Petty et al., 1990; Brenauer, 1985). The reduction of triphenyltetrazolium chloride to red formazan is an enzymatic process that occurs within mitochondria (Klein et al., 1981; Schaper and Schaper, 1983). The greater formation of red formazan following felbamate administration demonstrates the myocardial protective effect for felbamate at the mitochondrial level.

In accordance with the present invention, oral pretreatment with felbamate 100 or 300 mg/kg significantly reduced the expected rise in S-T segment elevation that followed coronary artery occlusion-reperfusion in the anesthetized rat. Several different drugs have been reported to inhibit or delay the expected rise in the S-T segment following coronary ligation or occlusion-reperfusion in animals. In the rat, these include: dexamethasone (Bernauer, 1980), verapamil (Bernauer, 1982), β-adrenoreceptor blocking agents pinololol, propranolol and metoprolol (Bernauer, 1985a) and RP 52891, a potassium channel activator (Grover et al., 1990).

Previous studies in the anesthetized dog have shown that intravenous administration of felbamate 50 to 200 mg/kg caused an immediate decrease in regional vascular resistance, blood pressure and heart rate. While the blood pressure and heart rate returned to baseline or slightly higher values and femoral and mesenteric blood flows increased, the regional vascular resistance remained at a level below baseline value. Such cardiovascular changes following the administration of felbamate (i.e., decrease in regional vascular resistance and increase in blood flow), may be influential factors that favor an increase in the endocardial/epicardial blood flow into the ischemic region of the myocardium. Such an action by felbamate is protective against the myocardial ischemic injury following occlusion-reperfusion in the anthesitized rat and, while not wishing to be bound by any theory, may be part of the protective myocardial mechanism of felbamate. The extent of ischemic myocardium that is potentially salvageable following coronary ligation or occlusion-reperfusion myocardial damage are critical factors that influence the degree to which drugs exert a cardioprotective action against the myocardial ischemic injury.

Summarizing the invention, it has been found that felbamate produces a cardioprotective effect against the myocardial injury that followed coronary artery occlusion-reperfusion in the anesthetized rat. Pretreatment with felbamate 100 or 300 mg/kg p.o. on each of three consecutive days prior to the induced ischemia significantly reduced the infarct size within the area at risk compared to vehicle. In addition, felbamate reduced the expected elevation in the S-T segment height that followed coronary ischemia.

Cardioprotective effects of drugs against myocardial ischemic injury is dependent upon the extent of ischemic myocardium that is potentially salvageable following coronary ligation or occlusion-reperfusion and the degree of endocardial-epicardial myocardial damage (Reimer et al., 1981; Hearse and Yellon, 1981; Hearse and Bolli, 1992). Recently, Kern (1992) reviewed the important role that calcium antagonists have in ameliorating the extent and duration of myocardial injury following infarction. Kern (1992) stated that the cardioprotective effects of the class of calcium antagonists may be through any one or a combination of several different mechanisms that include: direct cardioprotective effects, prevention of calcium accumulation in the mitochondria in ischemic cells, reduction in oxygen consumption or in coronary artery vasoconstriction or coronary spasm, prevention of ischemic-induced arrhythmias and increased coronary blood flow to ischemic tissue directly or through enhancement of collateral flow.

The cardioprotective mechanisms for calcium antagonists cited by Kern, 1992, may be considered as part of the protective action of several other classes of drugs against myocardial injury (Raina et al., 1978; Bernauer, 1980, 1985; Ferrari et al., 1988; Grover et al., 1988, 1990). While not wishing to be bound by any theory, it is believed that the cardioprotective effect of felbamate may involve one or more of these mechanisms.

The foregoing clearly demonstrates that:

1. Felbamate 100 or 300 mg/kg and vehicle (100) or vehicle (300) were each administered orally once on three consecutive days prior to experiment. The effects of felbamate compared to vehicle were determined on the following markers of myocardial injury following occlusion-reperfusion in the anesthetized rat: the infarct size and the change in the S-T segment elevation.

2. There was a significant formation of infarct within the area at risk following vehicle (100) (36.5±2.2%) and vehicle (300) (37.6±2.3%).

3. There was a significant decrease in the formation of infarct size compared to vehicle within the area at risk following felbamate 100 mg (36.5±2.2 versus 20.6±2.1%) and felbamate 300 mg (37.6±2.3 versus 15.3±1.4%).

4. There was a significant elevation from baseline S-T segment height during the entire 40 minute occlusion/60 minute reperfusion period following pretreatment with vehicle (100) or vehicle (300).

5. Pretreatment with felbamate 100 or 300 mg/kg on three consecutive days compared to vehicle each significantly reduced the S-T segment elevation throughout the entire 40 minute occlusion/60 minute reperfusion period.

6. The oral administration of felbamate 100 or 300 mg/kg on each of three consecutive days prior to occlusion and reperfusion caused a significant inhibition of the infarct size within the area at risk and a significant reduction compared to vehicle of the S-T segment elevation that followed coronary artery occlusion-reperfusion in the anesthetized rat. The significant inhibition by felbamate of two select markers that reflect myocardial injury following occlusion-reperfusion in the anesthetized rat demonstrates that felbamate has cardioprotective effects.

The compositions of the present invention may take any of a variety of forms although they are intended primarily for oral use and are suitable for forming into pills, capsules and tablets by well-known practices. When the active ingredient is in the form of a solid, a typical tablet composition comprises 2-phenyl-1,3-propanediol dicarbamate intermixed in a dry pulverulent state with suitable solid carriers and diluents.

Solid carriers and diluents suitable for use include sugars such as lactose and sucrose; cellulose derivatives such as carboxymethyl cellulose, ethyl cellulose, methyl cellulose, etc., gelatin including hard and soft gelatin capsules, talc, cornstarch, stearic acid and magnesium stearate.

The percentage of 2-phenyl-1,3-propanediol dicarbamate in the compositions may be varied over wide limits and the quantity of medicament furnished by each individual tablet or capsule is relatively unimportant since the indicated total daily dose can be reached by administering either one or a plurality of capsules or tablets.

Felbamate (2-phenyl-1,3-propanediol dicarbamate) has a very favorable preclinical profile characterized by a substantial margin of safety (protective index 16.9–19.1).

It should be understood that the above example is illustrative only of the invention herein disclosed. Given the present disclosure, it is anticipated that numerous variations will occur to those skilled in the art. A latitude of modification, substitution and change is intended and in some instances, some features of the invention will be employed without a corresponding use of other features. Accordingly, it is intended that the spirit and scope of the invention disclosed herein should be limited only by the following claims.

What is claimed is:

1. A method for the reduction and control of cellular damage following coronary artery occlusion-reperfusion in human or other warm-blooded animal patients which comprises administering to said patient in need of such treatment 2-phenyl-1,3-propanediol dicarbamate.

* * * * *